United States Patent [19]
Bochner et al.

[11] Patent Number: 6,046,020
[45] Date of Patent: Apr. 4, 2000

[54] USE OF ANTI-CAPSULE AGENTS IN MICROBIOLOGICAL TESTING

[75] Inventors: Barry Bochner, Alameda; Amalia Franco-Buff, Pleasanton, both of Calif.

[73] Assignee: Biolog, Inc., Calif.

[21] Appl. No.: 09/075,562

[22] Filed: May 5, 1998

[51] Int. Cl.⁷ .............................. C12Q 1/22; C12Q 1/18; C12Q 1/04
[52] U.S. Cl. ................................. 435/31; 435/32; 435/34
[58] Field of Search ........................... 435/34, 33, 252.1, 435/254.1, 810, 31, 32; 560/71, 143; 556/93, 92

[56] References Cited

U.S. PATENT DOCUMENTS

| | | | |
|---|---|---|---|
| 4,129,483 | 12/1978 | Bochner | 195/100 |
| 4,235,964 | 11/1980 | Bochner | 435/34 |
| 4,326,052 | 4/1982 | Kang et al. | 536/1 |
| 4,326,053 | 4/1982 | Kang et al. | 536/1 |
| 5,134,063 | 7/1992 | Bochner | 435/29 |
| 5,366,505 | 11/1994 | Farber | 623/11 |
| 5,384,176 | 1/1995 | Zimmerman et al. | 428/68 |
| 5,501,960 | 3/1996 | Dorn | 435/34 |
| 5,589,350 | 12/1996 | Bochner et al. | 435/29 |
| 5,607,741 | 3/1997 | Zimmerman et al. | 428/68 |
| 5,627,045 | 5/1997 | Bochner et al. | 435/34 |
| 5,669,446 | 9/1997 | Walker et al. | 166/300 |
| 5,669,447 | 9/1997 | Walker et al. | 166/300 |
| 5,683,713 | 11/1997 | Blank et al. | 424/449 |
| 5,716,406 | 2/1998 | Farber | 623/11 |

OTHER PUBLICATIONS

Domenico et al. Journal of Clinical Microbiology. (Nov. 1992), 30 (11), pp. 2859–1863.
Teichberg, et al. Journal of Infectious Diseases. (Jun. 1993), 167 (6), pp. 1501–1503.
Muller et al. Journal of Infectious Diseases. (Feb. 1998), 177 (2), pp. 501–503.
Bochner, "Sleuthing out Bacterial Identities," *Nature* 339:157–158 (1989).
Bochner, "'Breathprints' at the Microbial Level," *ASM News* 55:536–539 (1990).
Bochner and Savageau, "Generalized Indicator Plate for Genetic, Metabolic, and Taxonomic Studies with Microorganisms," *Appl. Environ. Microbiol.* 33:434–444 (1977).
Domenico et al., "Reduction of capsular polysaccharide and potentiation of aminoglycoside inhibition in Gram–negative bacteria by bismuth subsalicylate," *J. Antimicrob. Chemother.* 28: 801–810 (1991).
Muller et al., "Mechanism of Salicylate–Mediated Inhibition of Biofilm in *Staphylacoccus epidermidis*," *J. Infect. Dis.* 177: 501–503 (1998).
Roman et al., *ASM Abstracts* C–222, p. 379, American Society for Microbiology, Washington DC (1991).
Brock et al., *Biology of Microorganisms*, 7th ed., Prentice Hall, Englewood Cliffs, NJ, pp. 805–814 (1994).
Slack and Snyder, "Bacteria and Human Disease," pp. 30–32, 95–96, and 366, Year Book Medical Publishers, Inc. (1978).
Joklik et al. (eds.), *Zinsser Microbiology* Eighteenth Edition, pp. 18–19, 30–31, 69, 97–99, 479–482, 487 and 1115–1116, Appleton–Century–Crofts: Norwalk, Connecticut (1984).
Salton and Kim, "Structure," in *Medical Microbiology* Fourth Edition, Baron et al. (eds.), pp. 42–43, University of Texas Medical Branch at Galveston (1996).
Peterson, "Bacterial Pathogenesis," in *Medical Microbiology* Fourth Edition, Baron et al. (eds.), pp. 129–130, University of Texas Medical Branch at Galveston (1996).
Gilbert et al, "Inocula for Antimicrobial Sensitivity Testing: A Critical Review," *J. Antimicrob. Chemother.*, 20:147–154 (1987).
Reuters, "Best Way To Kill Bacteria? Stop Them Talking," Reuters America Inc. (Apr. 9, 1998).
Todd et al., "The Antifouling Activity of Natural and Synthetic Phenolic Acid Sulfate Esters," *Phytochem.*, 34:401–404 (1993).
Angell et al., "Mode of Action Studies on a Novel Antifouling Compound (p–Sulfoxy Coumaric Acid Isolated From Seagrass," *ASM Abstracts* N–217, p. 354, American Society for Microbiology, Washington DC (1994).
Arrage et al., "Efficacy Determination of Anti–Fouling and Foul Release Coatings Through the Non–Destructive Monitoring of Biofilm Biomass and Activity," *ASM Abstracts* N–218, p. 354, American Society of Microbiology, Washington DC (1994).
Franco–Buff et al., "Inhibition of Capsule Production in Bacteria By Thioglycolate," Poster Presentation, American Society for Microbiologists Annual Meeting (Jun. 1998).

*Primary Examiner*—Kathleen K. Fonda
*Attorney, Agent, or Firm*—Medlen & Carroll, LLP

[57] ABSTRACT

The present invention relates to growing and testing microorganisms in which an anti-capsule compound is used in order to prevent false positive results. The present invention is suited for the characterization of commonly encountered microorganisms which commonly produce capsules (e.g., Kkebsiella, Enterobacter, Escherichia, Burkholderia, Pseudomonas, Sphingobacterium, Chryseobacterium, Bacillus, Micrococcus, Staphylococcus, Haemophilus, Neisseria, Gordona, Kytococcus, Jonesia, Rhodococcus, Corynebacterium, Streptococcus, Cellulomonas, Brevibacterium, Arcanobacterium, Tsukamurella, Acinetobacter, Cryptococcus, etc.), as well as organisms of medical, veterinary, commercial, and/or industrial importance from various and diverse environments.

16 Claims, No Drawings

USE OF ANTI-CAPSULE AGENTS IN MICROBIOLOGICAL TESTING

FIELD OF THE INVENTION

The present invention relates to growing and testing microorganisms in which an anti-capsule compound is used in order to prevent false positive results. The present invention is suited for the characterization of commonly encountered microorganisms which commonly produce capsules (e.g., Klebsiella, Enterobacter, Escherichia, Burkholderia, Pseudomonas, Sphingobacterium, Chryseobacterium, Bacillus, Micrococcus, Staphylococcus, Haemophilus, Neisseria, Gordona, Kytococcus, Rhodococcus, Jonesia, Corynebacterium, Cellulomonas, Brevibacterium, Arcanobacterium, Tsukamurella, Acinetobacter, Cryptococcus, etc.), as well as organisms of medical, veterinary, commercial, and/or industrial importance from various and diverse environments.

BACKGROUND OF THE INVENTION

Under appropriate conditions, many bacterial species produce an extracellular polysaccharide-containing layer which forms a "capsule" up to 10 μm in thickness that surrounds the cells in a tight matrix. Some organisms produce a loose, amorphous "slime layer" that is more easily deformed than the relatively tight matrix of capsules. Slime layers also tend to be more easily deformed than capsules, and unlike capsules will not exclude particles. While the terms capsule and slime layer are often used in reference to these extracellular polysaccharide containing layers, some researchers refer to both structures as a "glycocalyx" (ie., glycocalyx is a more general term).

In addition to various polysaccharides and polysaccharide derivatives, the capsule may also contain glycoproteins. This capsule can be stained (e.g.,with Alcian blue) or be observed as a clear zone around the cells in an India ink wet mount. If the polysaccharide is soluble, it may diffuse throughout the culture media in which organisms are growing, forming slime, and making liquid media very viscous. The capsule may also help prevent desiccation of cells.

In vivo, capsular material is anti-phagocytic, and plays a role in pathogenicity of some organisms, including species such as *Streptococcus pyogenes, S. pneumoniae*, and *Bacillus anthracis*. In addition, glycocalyx material often plays important roles in pathogenesis, as it is involved in the attachment of microorganisms to host cells. In addition, capsular material allows microorganisms to attach to other surfaces, such as catheters and implants. Also, capsular material helps block the action of antimicrobials and causes biofouling in industrial processes. Thus, the production of extracellular capsular material provides microorganisms with virulence mechanisms, as well as allowing them to survive better in certain environments.

In addition to the pathogenesis implications of capsule production, capsular material often interferes with the metabolic reactions used to identify bacterial strains. With some organisms, such as Bacillus species, the problem is especially severe and the capsule can make it difficult to even obtain uniform suspensions of organisms for testing. Despite advances in technology, there remains a general need for systems that provide rapid and reliable biochemical identifications of microorganisms. For example, difficulties in identifying organisms of importance such as mucoid strains of *Pseudomonas cepacia* (now *Burkhrolderia cepacia*) in cystic fibrosis patients have occurred (See e.g,. Roman et al, ASM Abstracts, Abstract C-222, American Society for Microbiology, Washington, D.C., [1991], p. 379). In particular, it has been very difficult to develop an identification system which is capable of identifying various diverse types of organisms, while avoiding problems associated with the presence of capsular material produced by various organisms.

SUMMARY OF THE INVENTION

The present invention relates to growing and testing microorganisms in which an anti-capsule compound is used in order to prevent false positive results. The present invention is suited for the characterization of commonly encountered microorganisms which commonly produce capsules (e.g., Klebsiella, Enterobacter, Escherichia, Burkholderia, Pseudomonas, Sphingobacterium, Chryseobacterium, Bacillus, Micrococcus, Staphylococcus, Haemophilus, Neisseria, Gordona, Kytococcus, Rhodococcus, Jonesia, Corynebacterium, Streptococcus, Cellulomonas, Brevibacterium, Arcanobacterium, Tsukamurella, Acinetobacter, Cryptococcus, etc.), as well as organisms of medical, veterinary, commercial, and/or industrial importance from various and diverse environments.

The present invention provides methods inhibiting capsule production by microorganisms comprising the steps of: a) providing a sample suspected of containing microorganisms, wherein the microorganisms produce capsules; and an anti-capsule agent selected from the group consisting of thioglycolate, thioglycolate salts, thioglycolate esters, dihydroxyterephthalates, dihydroxyterephthalate salts, ibuprofen, and ibuprofen salts; and b) exposing the sample to the anti-capsule agent under conditions that production of capsules by the microorganisms is inhibited. In some particularly preferred embodiments, the dihydroxyterephthalate is 2,5-dihydroxyterephthalate. In further preferred embodiments, the concentration of anti-capsule agent is 1 to 10 mM, while in other particularly preferred embodiments, the concentration of anti-capsule agent is 2.5 to 5 mM.

In some preferred embodiments, the methods further comprise the step of testing the microorganisms. In alternative preferred embodiments of the methods, the testing comprises identifying the microorganisms. It is intended that the testing and/or identification steps incorporate any method suitable for the testing, detection, and/or identification of the microorganism. In other preferred embodiments of the method, the testing comprises determining the antimicrobial susceptibility of the microorganisms. It is intended that any number of antimicrobials will be tested using the methods of the present invention. Thus, it is not intended that the testing, identification, and or detection of the microorganisms in the methods of the present invention be limited to any particular format or testing panel. In particularly preferred embodiments of the methods, the microorganisms are selected from the group consisting of gram-negative bacteria, gram-positive bacteria, and fungi.

The present invention also provides methods for inhibiting capsule production by microorganisms comprising the steps of: a) providing a sample suspected of containing microorganisms, wherein the microorganisms produce capsules; a solid medium suitable for the growth of the microorganisms; and an anti-capsule agent; b) placing the anti-capsule agent on the solid medium to produce a treated medium; and c) inoculating the treated medium with the sample, under conditions that production of capsules by the microorganisms is inhibited, while the microorganisms grow.

In some preferred embodiments, the methods further comprise the step of testing the microorganisms. In alternative preferred embodiments of the methods, the testing comprises identifying the microorganisms. It is intended that the testing and/or identification steps incorporate any method suitable for the testing, detection, and/or identification of the microorganism. Thus, it is not intended that the testing, identification, and or detection of the microorganisms in the methods of the present invention be limited to any particular format or testing panel. In particularly preferred embodiments of the methods, the microorganisms are selected from the group consisting of gram-negative bacteria, gram-positive bacteria, and fungi. In particularly preferred embodiments of these methods, the anti-capsule agent is selected from the group consisting of thioglycolate, thioglycolate salts, thioglycolate esters, dihydroxyterephthalates, dihydroxyterephthalate salts, ibuprofer, ibuprofen salts, salicylates, and salicylate salts. In some particularly preferred embodiments, the dihydroxyterephthalate is 2,5-dihydroxyterephthalate. In further preferred embodiments, the concentration of anti-capsule agent is 1 to 10 mM, while in other particularly preferred embodiments, the concentration of anti-capsule agent is 2.5 to 5 mM.

The present invention also provides compositions comprising microorganisms and an anti-capsule agent selected from the group consisting of thioglycolate, thiglycolate salts, thioglycolate esters, dihydroxyterephthalates, and dihydroxyterephthalate salts. In particularly preferred embodiments, the microorganisms are selected from the group consisting of gram-negative bacteria, gram-positive bacteria, and fungi. In some particularly preferred embodiments, the dihydroxyterephthalate is 2,5-dihydroxyterephthalate. In further preferred embodiments, the concentration of anti-capsule agent is 1 to 10 mM, while in other particularly preferred embodiments, the concentration of anti-capsule agent is 2.5 to 5 mM.

The present invention also provides microbial test kits comprising at least one anti-capsule agent and a suspension medium. In one embodiment, the anti-capsule agent of the test kit is selected from the group consisting of thioglycolate, thioglycolate salts, thioglycolate esters, dihydroxyterephthalates, dihydroxyterephthalate salts, salicylates, salicylate salts, ibuprofen, and ibuprofen salts. In other embodiments, the test kit also comprises control organisms (i.e., organisms with known characteristics used in order to ensure that the test kit is working properly). In some particularly preferred embodiments, the dihydroxyterephthalate is 2,5-dihydroxyterephthalate. In further preferred embodiments, the concentration of anti-capsule agent is 1 to 10 mM, while in other particularly preferred embodiments, the concentration of anti-capsule agent is 2.5 to 5 mM. In yet other embodiments, the suspension medium is suitable for use as a growth medium (i.e., microorganisms will grow in the medium), as well as a suspension medium. In still other embodiments, the suspension medium is suitable for use as a diluent, in which a microbial suspensions is prepared for inoculation of a test panel. In still other embodiments, the test panel comprises one or more carbon sources useful for the identification of the microorganisms present in the suspension. In yet other embodiments, the test panel comprises one or more nitrogen sources useful for the identification of the microorganisms present in the suspension. In further embodiments, the test panel comprises both carbon and nitrogen sources useful for the identification of the microorganisms present in the suspension. It is not intended that the present invention be limited to any particular testing format or panel. Rather, it is intended that the present invention encompass any format or panel suitable for identification of microorganisms.

The present invention also provides methods for inhibiting biofilm formation, comprising the steps of: a) providing microorganisms, wherein the microorganisms are capable of forming a biofilm; a surface; and at least one anti-capsule agent selected from the group consisting of thioglycolate, thiglycolate salts, thioglycolate esters, dihydroxyterephthalate, dihydroxyterephthalate salts, ibuprofen, and ibuprofen salts; and b) exposing the surface to the anti-capsule agent under conditions such that biofilm formation by the microorganisms is inhibited. In some particularly preferred embodiments, the dihydroxyterephthalate is 2,5-dihydroxyterephthalate. In further preferred embodiments, the concentration of anti-capsule agent is 1 to 10 mM, while in other particularly preferred embodiments, the concentration of anti-capsule agent is 2.5 to 5 mM. In some embodiments of the method, the microorganisms are selected from the group consisting of gram-negative bacteria, gram-positive bacteria, and fungi.

The present invention also provides methods for enhancing the effectiveness of an antimicrobial agent, comprising the steps of: a) providing microorganisms; at least one antimicrobial; at least one anti-capsule agent selected from the group consisting of thioglycolate, thiglycolate salts, thioglycolate esters, dihydroxyterephthalates, dihydroxyterephthalate salts, ibuprofen, and ibuprofen salts; and b) exposing the microorganisms to at least one antimicrobial and at least one anti-capsule agent under conditions such that the effectiveness of the antimicrobial against the microorganisms is enhanced. In some particularly preferred embodiments, the dihydroxyterephthalate is 2,5-dihydroxyterephthalate. In further preferred embodiments, the concentration of anti-capsule agent is 1 to 10 mM, while in other particularly preferred embodiments, the concentration of anti-capsule agent is 2.5 to 5 mM. In some embodiments of the method, the microorganisms are killed, while in other embodiments, the microorganisms are inhibited. In preferred embodiments, the microorganisms are selected from the group consisting of gram-negative bacteria, gram-positive bacteria, and fungi. In yet other embodiments, the method also comprises identifying the microorganisms. In particular, it is contemplated that during in vitro testing of microorganisms for their susceptibility to the action of various antimicrobials, the microorganisms will concurrently be identified. In these embodiments, the testing panels used encompass identification substrates (e.g., carbon and/or nitrogen sources), as well as antimicrobial compounds suitable for in vivo and/or in vitro use. Thus, it is not intended that the methods of the present invention be limited to any particular setting. Indeed, it is intended that methods which increase antimicrobial effectiveness will find use in various settings, including but not limited to medical (e.g. in vivo treatment), veterinary (e.g., in vivo treatment), commercial, and/or industrial applications. It is intended that the methods of the present invention will find use in any number of settings in which it is desirable to increase antimicrobial effectiveness.

DESCRIPTION OF THE INVENTION

The present invention relates to growing and testing microorganisms in which an anti-capsule compound is used in order to prevent false positive results. The present invention is suited for the characterization of commonly encountered microorganisms which commonly produce capsules (e.g., Klebsiella, Enterobacter, Escherichia, Burkholderia, Pseudomonas, Sphingobacterium, Chryseobacterium, Bacillus, Micrococcus, Staphylococcus, Haemophilus, Neisseria, Gordona, Rhodococcus, Jonesia, Kytococcus, Corynebacterium, Streptococcus, Cellulomonas, Brevibacterium, Arcanobacterium, Tsukamurella, Acinetobacter, Cryptococcus, etc.), as well as organisms of medical, veterinary, commercial, and/or industrial importance from various and diverse environments.

In the development of the present invention, numerous compounds were tested for their ability to diminish capsule synthesis with their meg toxic to the organisms or their metabolic systems. In the most preferred embodiments, the present invention provides methods in which sodium thioglycolate is used to decrease capsular synthesis and facilitate identification of organisms.

A wide range of species were surveyed during the development of the present invention. Indeed, the present invention provides methods suitable for use with both gram-negative and gram-positive species, including, but not limited to Klebsiella, Enterobacter, Burkholderia, Pseudomonas, Sphingobacterium, Chryseobacterium, Bacillus, Micrococcus, Gordona, Rhodococcus, Corynebacterium, Cellulomonas, Brevibacterium, Arcanobacterium, and Tsukamurella. Direct assays of capsule content of a mucoid strain of K pneumoniae throughout a range of thioglycolate concentrations indicated that thioglycolate at concentrations of 0.03% (approx. 2.5 mM) and greater, are effective at inhibiting capsule synthesis. Higher concentrations are effective at inhibiting capsule synthesis, but also exhibit some toxicity.

In addition to growing cells in the presence of thioglycolate, in preferred embodiments of the methods of the present invention thioglycolate is spread onto the surface of agar culture media prior to streaking of cells (i.e., prior to inoculation), to enable the production of cell suspensions with evenly dispersed cells, without clumping or aggregation of cells. In other preferred embodiments of the methods, thioglycolate is added to cell suspensions prior to the inoculation of identification media and/or testing panels, in order to improve testing results.

During the development of the present invention, it was observed that organisms that produced capsules tended to exhibit false positive reactions in various identification procedures. Although an understanding of the exact mechanism of action is not necessary in order to use the invention, it was thought that these capsule-producing bacteria utilize their capsules as a carbon source, causing the false positive results observed in carbon source utilization test panels.

Although salicylate has been shown to be useful as an anti-capsule agent (See e.g., Domenico et al., J. Antimicrob. Chemother., 28: 801–810 [1991]), and as an inhibitor of biofilm production, during the development of the present invention, it was determined that sodium salicylate was only partially effective in inhibiting false positive results with gram-negative bacteria such as Klebsiella and Enterobacter. The bismuth salt of salicylate was also tested during the development of the present invention. However, this compound was found to be too toxic and poorly soluble for use in the preferred embodiments of the present invention.

In addition, some gram-negative bacteria, such as Burkholderia cepacia are capable of using salicylate as a carbon source. Thus, salicylate was determined to be less preferred agent for the elimination of false positive results with gram-negative bacteria. However, salicylate was found to be effective in reducing false positive reactions with gram-positive organisms. It was determined that none of the gram-positive organisms tested utilized sodium salicylate as a carbon source. Thus, sodium salicylate was found to be an excellent anti-capsule agent for various gram-positive organisms, including Micrococcus, Kytococcus, Rhodococcus, Jonesia, Cellulomonas, and Corynebacterium.

With both salicylate and thioglycolate, the optimal concentration was found to be 1 to 10 mM in preferred embodiments (i.e., in suspension). In most preferred embodiments, the concentration range is 2.5 to 5 mM. These agents can be either added to the suspension medium (e.g. saline [e.g., 0.85% NaCl], or PPS [Phytagel (0.01%), Pluronic F-68 (0.03%), and saline (0.45%)]), in which the cells are suspended prior to being inoculated into the testing panels, kits, materials, etc. In particularly preferred embodiments, 1 ml of a 50 to 100 mM stock solution of anti-capsule agent is added to 19 ml of a cell suspension.

Several thioglycolate analogs were also tested, as well as other compounds, including octylthioglycolate, iso-octylthioglycolate, octadeyl thioglycolate, n-butyl thioglycolate, ethyl thioglycolate, 2-mercaptopropionic acid, and 3-mercaptopropionic acid. However, most of these esters were not sufficiently water soluble, and all had a disagreeable odor. The only thioglycolate analog that was found to be partially effective was the ethyl ester; the structurally related acids, 2- and 3-mercaptopropionic acid were not as effective.

Ibuprofen, an anti-inflammatory agent with pharmacological effects similar to salicylate was also tested, and found to be partially effective as an anti-capsule agent for gram-negative and gram-positive bacteria. While ibuprofen (i.e., (S)-(+)-4-isobutyl-α-methylphenylacetic acid) was found to be a preferred compound, it is not intended that the present invention be so limited as other derivatives and analogs of the compound may be used in the present invention. Similarly, a wide variety of salicylate analogs were evaluated, the best of which was 2,5-dihydroxyterephthalate. Thus, in particularly preferred embodiments, the dihydroxyterephthalate of the present invention is 2,5-dihydroxyterephthalate. However, none of these agent worked as well as salicylate and thioglycolate for a wide range of bacteria.

The present invention also provides methods for preparation of suspensions of organisms that are suitable for use in inoculation of testing panels, kits, etc. These methods are particularly useful with organisms which tend to form aggregates or clumps when placed in suspension using methods known in the art. In these methods of the present invention, the capsule-inhibiting compound (e.g., thioglycolate) is swabbed onto the surface of the agar culture medium used to grow the culture to be tested prior to inoculation of the medium with the culture. The capsule-inhibiting compound prevents or inhibits the formation of pellicles (i.e., biofilms), allowing the production of uniform suspensions when the organisms are harvested from the solid medium and placed in solution. Embodiments of the present invention are particularly useful with spore-forming gram-positive organisms including but not limited to species such as those within the genus Bacillus. In preferred embodiments, 0.6% (50 mM) sodium thioglycolate was used. In other preferred embodiments, the methods use special media suitable for growing Bacillus, such as "BUG+maltose" (available from Biolog).

Thus, it is also contemplated that the present invention will find use in the inhibition or prevention of biofilms. For example, the present invention contemplates the use of thioglycolate, thioglycolate salts and analogs (e.g., octylthioglycolate, iso-octylthioglycolate, octadeyl thioglycolate, n-butyl thioglycolate, ethyl thioglycolate), as well as 2-mercaptopropionic acid, and 3-mercaptopropionic acid to prevent biofilm formation on medical devices such as catheters (See e.g., U.S. Pat. No. 5,716,406 to Farber, herein incorporated by reference).

It is further contemplated that other compounds with characteristics similar to those of salicylate and thioglycolate will find use in the methods of the present invention. For example, it is contemplated that amphiphilic, mucolytic, keratolytic, and anti-inflammatory small molecules with the ability to bind metals will be useful in the methods of the present invention. Indeed, it was determined that ibuprofen is also somewhat effective as an anti-capsule agent. Furthermore, it is contemplated that these compounds will find use in alternative embodiments of the present invention, such as in industrial and medical applications in prevention of biofilm formation (See e.g., Muller et al., J. Infect. Dis., 177: 501–503 [1998]).

It is also contemplated that the present invention will find use in providing compositions and means to increase the effectiveness of antimicrobials (e.g., treatment of cystic fibrosis patients colonized by mucoid organisms; See e.g., Domenico et al., J. Antimicrob. Chemother., 28: 801–810 [1991]). Thus, it is contemplated that in these embodiments, patients will be treated with anti-capsule agents in conjunction with other antimicrobials (e.g., antimicrobials in common use). In this manner, the anti-capsule agent facilitates the action of the antimicrobial by reducing the interference of the capsule to the action of the antimicrobial(s). In preferred embodiments, the anti-capsule agent is provided to the patient in a concentration of 1–10 mM, with a particularly preferred concentration range being 2.5–5 mM. These anti-capsule agents are provided to the patient using a regimen that provides the best conditions for antimicrobial activity. It is not intended that the present invention be limited to any particular disease condition or setting. Indeed, it is intended that the present invention be used in any disease condition or setting in which the administration of anti-capsular agents in vivo is warranted. It is also not intended that the present invention be limited to use with any particular antimicrobial compound(s). Thus, it is intended that the present invention be used in conjunction with any appropriate antimicrobial or antimicrobial combination, such that the activity of the antimicrobial is enhanced and/or the organisms associated with the animal's (e.g., a human patient) disease are killed or inhibited.

It is further contemplated that the present invention will be used in vitro, in order to assess the role of capsular material in pathogenesis, as well as other aspects of capsule production by various microorganisms. It is also intended that the present invention will be used alone or in conjunction with antimicrobial agents in industrial and commercial settings, in order to prevent or reverse biofilm formation. It is not intended that the present invention be limited to any particular setting or study. Rather, it is intended that the present invention will find use in any studies on capsular material, defects in capsule production, etc., including, but not limited to metabolic and other studies.

Although embodiments have been described with some particularity, many modifications and variations of the preferred embodiment are possible without deviating from the invention.

Definitions

The terms "sample" and "specimen" in the present specification and claims are used in their broadest sense. On the one hand, they are meant to include a specimen or culture. On the other hand, they are meant to include both biological and by environmental samples. These terms encompasses all types of samples obtained from humans and other animals, including but not limited to, body fluids such as urine, blood, fecal matter, cerebrospinal fluid (CSF), semen, and saliva, as well as solid tissue. These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

As used herein, the term "primary isolation" refers to the process of culturing organisms directly from a sample. Thus, primary isolation involves such processes as inoculating an agar plate from a culture swab, urine sample, environmental sample, etc. Primary isolation may be accomplished using solid or semi-solid agar media, or in liquid. As used herein, the term "isolation" refers to any cultivation of organisms, whether it be primary isolation or any subsequent cultivation, including "passage" or "transfer" of stock cultures of organisms for maintenance and/or use.

As used herein, the term "presumptive diagnosis" refers to a preliminary diagnosis which gives some guidance to the treating physician as to the etiologic organism involved in the patient's disease. Presumptive diagnoses are often based on "presumptive identifications," which as used herein refer to the preliminary identification of a microorganism based on observation such as colony characteristics, growth on primary isolation media, gram stain results, etc.

As used herein, the term "definitive diagnosis" is used to refer to a final diagnosis in which the etiologic agent of the patient's disease has been identified. The term "definitive identification" is used in reference to the final identification of an organism to the genus and/or species level.

Whether biological or environmental, a sample suspected of containing microorganisms may (or may not) first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be analyzed by the medium and method of the present invention.

As used herein, the term "culture" refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "organism" is used to refer to any species or type of microorganism, including but not limited to bacteria, yeasts and other fungi. As used herein, the term fungi, is used in reference to eukaryotic organisms such as the molds and yeasts, including dimorphic fungi.

As used herein, the term "spore" refers to any form of reproductive elements produced asexually (e.g., conidia) or sexually by such organisms as bacteria, fungi, algae, protozoa, etc. It is also used in reference to structures within microorganisms such as current and former members of the genus Bacillus (e.g., species which were previously included within the genus Bacillus, but have now been moved to another genus such as Paenibacillus), which provide advantages to the individual cells in terms of survival under harsh environmental conditions. It is not intended that the term be limited to any particular type or location of spores, such as "endospores" or "exospores." Rather, the term is used in the very broadest sense.

As used herein, the term "capsule" refers to extracellular material in a relatively tight matrix that resists the passage of materials into the cell, while the term "slime layer" refers to an amorphous layer surrounding the cell that does not prevent the passage materials into the cell. As used herein, the term "glycocalyx" refers to both capsules and slime layers, as well as any other polysaccharide-containing extracellular material that surrounds some cells. It is not intended that the present invention be limited to any particular capsule-producing species. Indeed, the present invention encompasses capsule-producing bacteria as well as fungi.

As used herein, the terms "microbiological media" and "culture media," and "media" refer to any substrate for the growth and reproduction of microorganisms. "Media" may be used in reference to solid plated media which support the growth of microorganisms. Also included within this definition are semi-solid and liquid microbial growth systems including those that incorporate living host organisms, as well as any type of media.

As used herein, the term "carbon source" is used in reference to any compound which may be utilized as a source of carbon for bacterial growth and/or metabolism. Carbon sources may be in various forms, including, but not limited to polymers, carbohydrates, acids, alcohols, aldehydes, ketones, amino acids, and peptides.

As used herein, the term "nitrogen source" is used in reference to any compound which may be utilized as a source of nitrogen for bacterial growth and/or metabolism. As with carbon sources, nitrogen sources may be in various forms, such as free nitrogen, as well as compounds which contain nitrogen, including but not limited to amino acids, peptones, vitamins, and nitrogenous salts.

As used herein, the term "antimicrobial" is used in reference to any compound which inhibits the growth of, or kills microorganisms. It is intended that the term be used in its broadest sense, and includes, but is not limited to compounds such as antibiotics which are produced naturally or synthetically. It is also intended that the term includes compounds and elements that are useful for inhibiting the growth of, or killing microorganisms. "Antimicrobial susceptibility tests" are conducted in order to determine whether a microorganism is susceptible to the effects of an antimicrobial.

As used herein, the term "testing substrate" is used in reference to any carbon and/or nitrogen source that may be utilized to differentiate bacteria based on biochemical characteristics. For example, one bacterial species may utilize one testing substrate that is not utilized by another species. This utilization may then be used to differentiate between these two species. It is contemplated that numerous testing substrates be utilized in combination. Testing substrates may be tested individually (e.g., one substrate per testing well or compartment, or testing area) or in combination (e.g., multiple testing substrates mixed together and provided as a "cocktail").

Following exposure to a testing substrate such as a carbon or nitrogen source, or an antimicrobial, the response of an organism may be detected. This detection may be visual (i.e., by eye) or accomplished with the assistance of machine (s) (e.g., the Biolog MicroStation Readers™). For example, the response of organisms to carbon sources may be detected as turbidity in the suspension due to the utilization of the testing substrate by the organisms. Likewise, growth can be used as an indicator that an organism is not inhibited by certain antimicrobials. In one embodiment, color is used to indicate the presence or absence of organism growth/metabolism.

As used herein, the terms "chromogenic compound" and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator" encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator" and "oxidation-reduction indicator" encompass all compounds commonly used for detection of oxidation/reduction potentials (i.e., "eH") including, but not limited to various types or forms of tetrazolium, resazurin, methylene blue, and quinone-imide redox dyes including the compounds known as "methyl purple" and derivatives of methyl purple. The quinone-imide redox dye known as methyl purple is referred to herein as "redox purple." In a particularly preferred embodiment, "redox purple" comprises the compound with the chemical structure shown in FIG. 5, VI. It is contemplated that analogous derivatives of the reagent (e.g., alkali salts, alkyl O-esters), with modified properties (e.g., solubility, cell permeability, toxicity, and/or modified color(s)/absorption wavelengths) will be produced using slight modifications of the methods described in Example 13. It is also contemplated that various forms of redox purple (e.g., salts, etc.), may be effectively used in combination as a redox indicator in the present invention.

As used herein, the terms "testing means" and "testing device" are used in reference to testing systems in which at least one organism is tested for at least one characteristic, such as utilization of a particular carbon source, nitrogen source, or chromogenic substrate, and/or susceptibility to an antimicrobial agent. This definition is intended to encompass any suitable means to contain a reaction mixture, suspension, or test. It is intended that the term encompass microtiter plates, petri plates, microcard devices, or any other supporting structure that is suitable for use. For example, a microtiter plate having at least one gel-initiating agent included in each of a plurality of wells or compartments, as disclosed in pending U.S. Pat. No. 5,627,045, and U.S. patent appln. Ser. No. 08/762,656, both of which are herein incorporated by reference, comprise testing means suitable for use with the present invention. Other examples of testing means include microtiter plates without gel-initiating means included in the well (See e.g., U.S. Pat. No. 5,589,350, and pending U.S. patent appln. Ser. No. 08/685,695, both of which are hereby incorporated by reference).

It is also intended that other compounds such as carbon sources or antimicrobials will be included within the compartments. The definition is also intended to encompass a "microcard" or miniaturized plates or cards which are similar in function, but much smaller than standard microtiter plates (for example, many testing devices can be conveniently held in a user's hand). It is not intended that the present invention be limited to a particular size or configuration of testing device or testing means. For example, it is contemplated that various formats will be used with the present invention, including, but not limited to microtiter plates, microcards, petri plates, petri plates with internal dividers used to separate different media placed within the plate, test tubes, as well as many other formats.

As used herein, the term "gelling agent" is used in a broad generic sense, and includes compounds that are obtained from natural sources, as well as those that are prepared synthetically. As used herein, the term refers to any substance which becomes at least partially solidified when certain conditions are met. For example, one gelling agent encompassed within this definition is Gelrite™, a gellan which forms a gel upon exposure to divalent cations (e.g., $Mg^{2+}$ or $Ca^{2+}$). Gelrite™ is produced by deacetylating a natural polysaccharide produced by *Pseudomonas elodea*, and is described in U.S. Pat. No. 5,627,045, and pending U.S. patent appln. Ser. No. 08/762,656; and described by Kang et al. in U.S. Pat. Nos. 4,326,052 and 4,326,053; all of which are herein incorporated by reference).

Included within the definition are various gelling agents obtained from natural sources, including protein-based as well as carbohydrate-based gelling agents. One example is bacteriological agar, a polysaccharide complex extracted from kelp. Also included within the definition are such compounds as gelatins (e.g., water-soluble mixtures of high molecular weight proteins obtained from collagen), pectin (e.g., polysaccharides obtained from plants), carrageenans and alginic acids (e.g., polysaccharides obtained from seaweed), and gums (e.g., mucilaginous excretions from some plants and bacteria). It is contemplated that various carrageenan preparations will be used in the present invention, with iota carrageenan comprising a preferred embodiment. It is also contemplated that gelling agents used in the present invention may be obtained commercially from a supply company, such as Difco, BBL, Oxoid, Marcor, Sigmna, or any other source.

It is not intended that the term "gelling agent" be limited to compounds which result in the formation of a hard gel substance. A spectrum is contemplated, ranging from merely a more thickened or viscous colloidal suspension to one that is a firm gel. It is also not intended that the present invention be limited to the time it takes for the suspension to gel.

Importantly, it is intended that the present invention provides a gelling agent suitable for production of a matrix in which organisms may grow (i e., a "gel matrix"). The gel matrix of the present invention is a colloidal-type suspension of organisms produced when organisms are mixed with an aqueous solution containing a gelling agent, and this suspension is exposed to a gel-initiating agent. It is intended that this colloidal-type gel suspension be a continuous matrix medium throughout which organisms may be evenly dispersed without settling out of the matrix due to the influence of gravity. The gel matrix must support the growth of organisms within, under, and on top of the gel suspension.

As used herein the term "gel-initiating agent" refers to any compound or element which results in the formation of a gel matrix, following exposure of a gelling agent to certain conditions or reagents. It is intended that "gel-initiating agent" encompass such reagents as cations (e.g., $Ca^{2+}$, $Mg^{2+}$, and $K^+$). Until the gelling agent contacts at least one gel-initiating agent, any suspension containing the gelling agent remains "ungelled" (i.e., there is no thickening, increased viscosity, nor hardening of the suspension). After contact, the suspension will become more viscous and may or may not form a rigid gel (i.e., contact will produce "gelling").

As used herein, the term "inoculating suspension" or "inoculant" is used in reference to a suspension which may be inoculated with organisms to be tested. It is not intended that the term "inoculating suspension" be limited to a particular fluid or liquid substance. For example, inoculating suspensions may be comprised of water, saline, or an aqueous solution which includes at least one gelling agent. It is also contemplated that an inoculating suspension may include a component to which water, saline or any aqueous material is added. In particularly preferred embodiments, once the inoculating suspension contains microorganisms, this suspension is used to inoculate test panels for the identification, testing, and/or detection of the microorganisms present in the sample. In addition, it is intended that the inoculating suspension be used to determine the antimicrobial susceptibility of microorganisms and/or used in a manner so as to increase the effectiveness of antimicrobial agents (i.e., when the inoculating suspension also contains at least one anti-capsule agent).

As used herein, the term "test kit" is used in reference to a combination of reagents and other materials. It is contemplated that the kit may include reagents such as carbon sources, nitrogen sources, chromogenic substrates, antimicrobials, diluents and other aqueous solutions, as well as microplates (e.g., GN, GP, YT, SF-N, SF-P, and other MicroPlates™, obtained from Biolog), inoculants, microcards, and plated agar media. The present invention contemplates other reagents useful for the growth, identification and/or determination of the antimicrobial susceptibility of microorganisms. For example, the kit may include reagents for detecting the growth of microorganisms following inoculation of kit components (e.g,tetrazolium or resazurin included in some embodiments of the present invention). It is not intended that the term "test kit" be limited to a particular combination of reagents and/or other materials. Further, in contrast to methods and kits which involve inoculating organisms on or into a preformed matrix such as an agar surface or broth, the present invention involves inoculation of a testing plate in which the organisms are suspended within a gel-forming matrix.

As used herein, the term "test panel" refers to any combination of testing substrates useful for the identification microorganisms. For example, it is intended that the term encompass testing panels such as the Biolog MicroPlates™, in which the detection of carbon source utilization is used to identify organisms- In preferred embodiments, the test panel includes a multi-well test plate. The wells of the multi-well test plate contain various substrates useful for the detection and/or identification of the microorganism of interest. An "antimicrobial test panel" is used to determine whether a microorganism is susceptible to the effects of at least one antimicrobial.

With any of the testing formats, the visual result that is detected by eye or by instrument can be any optically perceptible change such as a change in turbidity, a change in color, or the emission of light, such as by chemiluminescence, bioluminescence, or by Stokes shift. Color indicators may be, but are not limited to, redox indicators (e.g., tetrazolium, resazurin, and/or redox purple), pH indicators, or various dyes and the like. Various dyes are described in U.S. Pat. Nos. 4,129,483, 4,235,964 and 5,134,063 to Bochner, hereby incorporated by reference. See also, Bochner, Nature 339: 157 (1989); and ASM News 55: 536 (1990). A generalized indicator useful for practice of the present invention is also described by Bochner and Savageau (See, Bochner and Savageau, Appl. Environ. Microbiol., 33: 434 [1977]).

Testing based on the redox technology is extremely easy and convenient to perform. A cell suspension is prepared and introduced into the testing compartments of the device. Each compartment is prefilled with a different substrate.

In a preferred embodiment, all wells are prefilled with test formula comprising a basal medium that provides nutrients for the microorganisms, and a color-change indicator, and each compartment is prefilled with a different carbon compound or "testing substrate," against which the microorganism is tested. "Basal medium," as used herein, refers to a medium which provides nutrients for the microorganisms, but does not contain sufficient concentrations of carbon compounds to trigger a color response from the indicator. "Carbon compound," "carbon source" and "testing substrate" are equivalent terms, and are used interchangeably herein to refer to a carbon chemical in sufficient concentration as to trigger a color response from the indicator when it is utilized (metabolized) by a microorganism (e.g., GN, GP, YT, and other MicroPlates™ commercially available from Biolog). In a particularly preferred embodiment, redox purple is used as a redox indicator in the present invention.

One of the principal uses of the present invention is as a method and device for simple testing and speciation of microorganisms. The present invention contemplates microbiological testing based on the redox technology discussed above wherein a sample of a pure culture of microorganism is removed from a culture medium on which it has been grown and suspended in saline or water at a desired density. This suspension is then introduced into the compartments of the testing device which have been prefilled with basal medium, indicator, and substrate chemicals. The method is extremely easy and convenient to perform, and, unlike other approaches, the method and device do not require skilled personnel and cumbersome equipment.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); °C (degrees Centigrade); (S)-(+)-4-isobutyl-$\alpha$-methylphenylacetic acid (ibuprofen); BBL (Becton Dickinson Microbiology Systems, Cockeysville, Md.); DIFCO (Difco Laboratories, a division of Becton Dickson); Sigma (Sigma Chemical Co., St. Louis, Mo.); Aldrich (Aldrich Chemical Co., Milwaukee, Wis.); Biolog (Biolog, Inc., Hayward, Calif.); ATCC (American Type Culture Collection, Rockville, Md.); API (API Analytab Products, a division of Biomerieux); and Biomerieux (Biomerieux, Hazelwood, Mo.).

The following Table lists the principal bacterial strains used in the following Examples. In addition to these organisms, other species were also tested during the development of the present invention; this list is simply intended to provide examples of organisms tested. The numbers used in this Table refer to the numbers assigned to these cultures in the Biolog culture collection. For some species, more than one strain was used. For example, one strain *K pneumoniae* (Biolog #5008) is a relatively non-mucoid strain, while another strain (Biolog #1043) is a highly mucoid strain. In addition, two *P. aeruginosa* strains were used; (Biolog #1191) is a non-mucoid strain, while 13363 is a mucoid strain. These organisms are available from Biolog.

TABLE 1

| Organisms Tested | |
| --- | --- |
| Organism | Biolog Number |
| Enterobacter aerogenes | 4303 |
| Klebsiella pneumoniae | 5008 |
| Klebsiella pneumoniae | 1043 |
| Pseudomonas aeruginosa | 1191 |
| Pseudomonas aeruginosa | 13363 |
| Chryseobacterium indologenes | 1791 |
| Micrococcus lylae | 6823 |
| Micrococcus luteus | 9061 |
| Kytococcus sedentarius | 14080 |
| Bacillus mycoides | 9257 |

EXAMPLE 1

Testing of Gram-Negative Organisms

In this Example, 2.5 mM and 5 mM each of thioglycolate, sodium salicylate, and ibuprofen were tested with various Gram-negative organisms to determine the anti-capsule activity of the compounds. In these experiments, the test compounds were added to PPS suspensions of organisms, and the suspensions were then used to inoculate Biolog GN plates (Biolog) used to identify grain-negative organisms, incubated overnight at 35° C. (or 30° C. for *C. indologenes*). In the following Table, "++" indicates that a strong false positive reaction was observed in the negative control well of the GN plate, while "+" indicates a moderate false positive, "−" indicates that no false positive reaction was observed, "+/−" indicates an equivocal reaction, and "pi" indicates that the true positive reactions were partially inhibited. In this Table, the column labelled "No Additions" was the control in which no anti-capsule compound was added.

TABLE 2

Results With Gram-Negative Organisms

| | | Thioglycolate | | Salicylate | | Ibuprofin | |
|---|---|---|---|---|---|---|---|
| Strain | No Additions | 2.5 mM | 5 mM | 2.5 mM | 5 mM | 2.5 mM | 5 mM |
| E. aerogenes (4303) | ++ | +/– | – | +/– (pi) | +/– (pi) | +/– | +/– |
| K. pneumoniae (5008) | ++ | – | – | – (pi) | – (pi) | + (pi) | + |
| K. pneumoniae (1043) | ++ | – | – | – (pi) | – (pi) | + | – |
| P. aeruginosa (1191) | – | – | – (pi) | – | – (pi) | – (pi) | – (pi) |
| P. aeruginosa (13363) | – | – | – (pi) | – | – | – | – |
| C. indologenes (1791) | ++ | + | +/– | ++ | ++ | +m/– (pi) | – (pi) |

EXAMPLE 2

Testing of Gram-Positive Organisms

In this Example, various gram-positive organisms were tested using 2.5 mM and 5 mM thioglycolate, thioglycolate ethyl ester, salicylate, and ibuprofen. The same methods as described in Example 1 were used, with the exception being that Biolog GP plates were used, and all of the organisms were incubated at 30° C. In addition, B. mycoides was grown on BUG medium containing 0.25% maltose, and BUGM medium containing 1% glucose (both of these media are available from Biolog). The results are shown in Table 3. The same indicators as used in Table 2, above (Example 1) are used in Table 3. In this Table, "NT" indicates that the compound was not tested, and "NR" indicates that no reaction was observed, due to the toxicity of the compound for the organism tested.

In these experiments, sodium thioglycolate (0.6%; 50 mM) was swabbed onto the surface of the agar medium (BUG with maltose and BUGM with glucose, both of which are available from Biolog) used to grow Bacillus species prior to inoculating the plate with the culture to be tested. After swabbing, the anticapsular agent was allowed to be absorbed into the medium prior to inoculation with the microbial culture to be tested. Examples of Bacillus species that are among the most problematic due to capsule production are B. licheniformis (e.g. Biolog strains #9251, 9754, and 11101), which forms very mucoid growth often overlaid with a skin-like pellicle, and B. subtilis (e.g., Biolog strain #9265), which produces very dry, crusty aggregates. These strains (as well as numerous others) adhere tightly to the agar surface and/or clump strongly, making them difficult to remove from the agar and suspend in a solution. Thus, the growth characteristics of these and other organisms make it very difficult to test and/or identify these organisms.

In these experiments, it was determined that thioglycolate greatly diminished the formation of mucoid slimes, pellicles, or crusty-looking aggregates (i.e., biofilms) on the agar surfaces. While an understanding of the mechanism is not necessary in order to use the present invention, it is thought that these types of capsular manifestations promote attachment and aggregation of microbial cells present on surfaces to form biofilms. Organisms grown using this method also provided uniform cell suspensions when placed in liquid media or diluents. In contrast, when these biofilm-producing organisms were grown using methods known in the art (i.e., without thioglycolate), the suspensions are not uniform as the cells tend to aggregate and/or form non-dispersable clumps. It is contemplated that these methods will find use with other biofilm-producing gram-positive and gram-negative organisms, as the present invention clearly provides methods to prevent or inhibit the formation of biofilms such as pellicles.

EXAMPLE 4

Testing of Fungi

In this Example, anti-capsule agents are tested with various fungal species. In particular, fungi such as Cryptococcus

TABLE 3

Results With Some Gram-Positive Organisms

| | | Thioglycolate | | Thioglycolate Ethyl Ester | | Salicylate | | Ibuprofin | |
|---|---|---|---|---|---|---|---|---|---|
| Strain | No Additions | 2.5 mM | 5 mM | 2.5 mM | 5 mM | 2.5 mM | 5 mM | 2.5 mM | 5 mM |
| M. lylae | +/– | +/– | + | + | + | +/– | +/– | – | – |
| M. luteus | +/– | + | + (pi) | + (pi) | + (pi) | – to +/– | – to +/– | +/– (pi) | +/– (pi) |
| K. sedentarius | + | NT | NT | NT | NT | – | +/– | + | – (pi) |
| B. mycoides grown on BUG with maltose | – | – | – | – (pi) | – (pi) | – (pi) | – (pi) | NR | NR |
| B. mycoides grown on BUGM with glucose | ++ | NT | NT | NT | NT | NT | NT | NT | NT |

EXAMPLE 3

Growth of Gram-Positive Organisms on Solid Media

In addition to testing the anti-capsule compounds in suspensions used to inoculate the GP plates as described in Example 2, in this Example, anti-capsule agents were also tested for their ability to inhibit biofilm production by organisms that tend to form mucoid slime, pellicles, or crusty-appearing aggregates on solid media.

and Aureobasidium, are used in these experiments. These fungi are grown on media suitable for their growth (e.g., malt extract agar, potato dextrose agar, or other media) under conditions suitable for fungal growth. A suspension of fungal cells is prepared by transferring some of the growth into a water, saline, or gelling (e.g., 0.25% phytagel) solution. The anti-capsule agent (e.g., thioglycolate, salicylate, ibuprofen) is added to the solution as described in the above Examples. This suspension is then used to inoculate a testing panel suitable for the testing and/or identification of fungi (e.g., Biolog YT MicroPlate™), and incubated for approximately one to four days at approximately 26° C. (i.e., incubation occurs for an amount of time suitable for the particular organism to be identified). The negative control wells (e.g., wells A1 and D1 in the Biolog YT MicroPlate™) are used as a basis to assess the growth (e.g., turbidity) in the other wells of the testing panel (e.g., microplate); these wells contain a variety of carbon sources.

From the above Examples, it is clear that the present invention provides unexpected and much improved methods for the rapid biochemical testing of microorganisms, in many uses and formats (or configurations) and in particular, provides a major advance in the testing of capsule-producing microorganisms. The present invention provides advantages to both automated and manual systems for identification of microorganisms. For example, the results may be observed visually (i.e., by eye) by the person conducting the test, without assistance from a machine. Alternatively, the results may be obtained with the use of equipment (e.g., a microplate reader) that measures transmittance, absorbance, or reflectance through, in, or from each well of a multitest device such as microplate or microcard. These advantages enhance the speed and accuracy of scoring test results in studies to characterize and/or identify microorganisms.

What is claimed is:

1. A method for inhibiting capsule production by microorganisms comprising the steps of:
   a) providing:
      i) a sample containing microorganisms, wherein said microorganisms produce capsules; and
      ii) an anti-capsule agent selected from the group consisting of thioglycolate, thioglycolate salts, and thioglycolate esters; and
   b) exposing said sample to said anti-capsule agent under conditions that production of capsules by said microorganisms is inhibited.

2. The method of claim 1, comprising the further step of testing said microorganisms.

3. The method of claim 2, wherein said testing comprises identifying said microorganisms.

4. The method of claim 2, wherein said testing comprises antimicrobial susceptibility testing.

5. The method of claim 1, wherein said microorganisms are selected from the group consisting of gram-negative bacteria, gram-positive bacteria, and fungi.

6. A method for inhibiting capsule production by microorganisms comprising the steps of:
   a) providing:
      i) a sample containing microorganisms, wherein said microorganisms produce capsules;
      ii) a solid medium suitable for the growth of said microorganisms; and
      ii) an anti-capsule agent, selected from the group consisting of thioglycolate, thioglycolate salts, and thioglycolate esters;
   b) placing said anti-capsule agent on the solid medium to produce a treated medium; and
   inoculating treated medium with said sample under conditions that production of capsules by said microorganisms is inhibited, while said microorganisms grow.

7. The method of claim 6, comprising the further step of testing said microorganisms.

8. The method of claim 7, wherein said testing comprises identifying said microorganisms.

9. The method of claim 6, further providing at least one antimicrobial agent.

10. The method of claim 6, wherein said microorganisms are selected from the group consisting of gram-negative bacteria, gram-positive bacteria, and fungi.

11. A microbial test kit comprising at least one anti-capsule agent selected from the group consisting of thioglycolate, thioglycolate salts, and thioglycolate esters, an inoculating suspension medium, and a multi-well test panel.

12. The microbial test kit of claim 11, wherein said anti-capsule agent has a concentration of 1 to 10 mM.

13. The microbial test kit of claim 11, wherein said anti-capsule agent has a concentration of 2.5 to 5 mM.

14. The microbial test kit of claim 11, wherein said test panel comprises one or more substrates selected from the group consisting of carbon sources and nitrogen sources.

15. A method for inhibiting biofilm formation, comprising the steps of:
   a) providing:
      i) microorganisms, wherein said microorganisms are capable of forming a biofilm;
      ii) a surface; and
      iii) at least one anti-capsule agent selected from the group consisting of thioglycolate, thioglycolate salts, and thioglycolate esters; and
   b) exposing said surface to said anti-capsule agent under conditions such that biofilm formation by said microorganisms is inhibited.

16. The method of claim 15, wherein said microorganisms are selected from the group consisting of gram-negative bacteria, gram-positive bacteria, and fungi.

* * * * *

UNITED STATES PATENT AND TRADEMARK OFFICE
CERTIFICATE OF CORRECTION

PATENT NO. : 6,046,020
DATED : April 4, 2000
INVENTOR(S) : Barry Bochner

It is certified that error appears in the above-identified patent and that said Letters Patent is hereby corrected as shown below:

Title page,
ABSTRACT, LINE 6, please delete "Kkebsiella" and insert -- Klebsiella --.

Column 3,
Line 18, please delete "ibuprofer" and insert -- ibuprofen --.

Column 5,
Line 11, please delete "with their meg" and insert -- without being --.

Column 14,
Line 56, please delete "grain-negative" and insert -- gram-negative --.

Tables,
Column 15, table 2, please delete the following data:

| Strain | No Additions | Thioglycolate | | Salicylate | | Ibuprofen | |
|---|---|---|---|---|---|---|---|
| | | 2.5 mM | 5 mM | 2.5 mM | 5 mM | 2.5 mM | 5 mM |
| K. pneumoniae (5008) | ++ | - | - | - (pi) | - (pi) | + (pi) | + |
| C. indologenes (1791) | ++ | + | +/- | ++ | ++ | +m/- (pi) | - (pi) |

UNITED STATES PATENT AND TRADEMARK OFFICE
CERTIFICATE OF CORRECTION

PATENT NO. : 6,046,020
DATED : April 4, 2000
INVENTOR(S) : Barry Bochner

It is certified that error appears in the above-identified patent and that said Letters Patent is hereby corrected as shown below:

and substitute the following data:

| Strain | No Additions | Thioglycolate | | Salicylate | | Ibuprofen | |
|---|---|---|---|---|---|---|---|
| | | 2.5 mM | 5 mM | 2.5 mM | 5 mM | 2.5 mM | 5 mM |
| K. pneumoniae (5008) | ++ | - | - | - (pi) | - (pi) | + | + |
| C. indologenes (1791) | ++ | + | +/- | ++ | ++ | +/- (pi) | - (pi) |

Claims,
Column 18, claim 6,
Line 9, please delete "inoculating" and insert
-- c) inoculating --.

Signed and Sealed this

Twenty-fifth Day of December, 2001

Attest:

Attesting Officer

JAMES E. ROGAN
Director of the United States Patent and Trademark Office